(12) United States Patent
Nabeta et al.

(10) Patent No.: US 10,674,977 B2
(45) Date of Patent: Jun. 9, 2020

(54) RADIOGRAPHIC IMAGING APPARATUS

(71) Applicant: FUJIFILM Corporation, Tokyo (JP)

(72) Inventors: Toshiyuki Nabeta, Kanagawa (JP); Fumito Nariyuki, Kanagawa (JP); Masayoshi Matsuura, Kanagawa (JP); Ryosuke Ogura, Kanagawa (JP); Haruyasu Nakatsugawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 213 days.

(21) Appl. No.: 15/846,864

(22) Filed: Dec. 19, 2017

(65) Prior Publication Data
US 2018/0116617 A1 May 3, 2018

Related U.S. Application Data

(63) Continuation of application No. PCT/JP2016/002887, filed on Jun. 15, 2016.

(30) Foreign Application Priority Data

Jun. 22, 2015 (JP) .................. 2015-124511

(51) Int. Cl.
*H05G 1/02* (2006.01)
*A61B 6/00* (2006.01)

(52) U.S. Cl.
CPC .............. *A61B 6/4452* (2013.01); *A61B 6/40* (2013.01); *A61B 6/4458* (2013.01); *A61B 6/4405* (2013.01)

(58) Field of Classification Search
CPC ....... A61B 6/40; A61B 6/4405; A61B 6/4452; A61B 6/4458; A61B 6/107; A61B 6/4429;
(Continued)

(56) References Cited

U.S. PATENT DOCUMENTS 5,835,558 A * 11/1998 Maschke .............. A61B 6/4233
378/198
5,901,200 A * 5/1999 Krause ................. A61B 6/4405
378/197
(Continued)

FOREIGN PATENT DOCUMENTS

CN 101347336 A 1/2009
CN 104068879 A 10/2014
(Continued)

OTHER PUBLICATIONS

Toshiba Medical Supply Co., Ltd., "Portable X-ray Equipment IPF-21", [online], [Search on Jul. 30, 1999], Internet URL: http://www.toshiba-ryouyouhin.co.jp/tmeds/xrays/ipf21.html, total 4 pages.
(Continued)

*Primary Examiner* — Irakli Kiknadze
(74) *Attorney, Agent, or Firm* — Sughrue Mion, PLLC

(57) ABSTRACT

A radiographic imaging apparatus comprises: a leg unit that is capable of traveling on an apparatus-placement surface by a wheel unit; a body unit that is held on the leg unit; an arm unit that is connected to the body unit and is capable of protruding upward from the body unit; and a radiation source that is mounted on the arm unit, wherein the arm unit includes a body-side part that is capable of extending and retracting in a direction of the protruding of the arm unit and is connected to the body unit, and a radiation source-side part on which the radiation source is mounted, the radiation source-side part is connected to a distal end side of the body-side part so as to be revolvable in a direction where an angle between the radiation source-side part and the body-side part changes, and revolution regulating unit.

12 Claims, 13 Drawing Sheets

(58) Field of Classification Search
CPC ....... A61B 6/447; A61B 6/547; A61B 6/4441; A61B 6/548; A61B 6/035; A61B 6/102; A61B 6/4423; A61B 6/027; A61B 6/105; A61B 6/00; A61B 6/462; A61B 6/563; A61B 90/50; A61B 6/0457; A61B 6/4283; A61B 6/4464; A61B 6/4476; A61B 6/467; A61B 6/588; A61B 6/463; G01N 23/00; G01N 2223/301; G01N 23/04; G01N 2223/639; G01N 2223/407; G01N 2223/419; G01N 2223/628; G01N 2223/631; G01N 2223/646; G01N 23/046; G01N 23/18; G01T 7/00; H05G 1/02; H05G 1/60; H05G 1/64
USPC .................................................... 378/62, 197
See application file for complete search history.

(56) References Cited

U.S. PATENT DOCUMENTS

| | | | | |
|---|---|---|---|---|
| 6,179,257 | B1* | 1/2001 | Ueno | F16F 1/18 16/30 |
| 7,611,282 | B2* | 11/2009 | Koren | A61B 6/4233 378/198 |
| 8,690,425 | B2* | 4/2014 | Kopcienski | A61B 6/4405 378/102 |
| 9,326,747 | B2 | 5/2016 | Omura | |
| 2014/0093040 | A1 | 4/2014 | Omura | |
| 2014/0233703 | A1* | 8/2014 | Omura | A61B 6/4405 378/98 |
| 2014/0291539 | A1 | 10/2014 | Omura | |
| 2015/0069256 | A1 | 3/2015 | Nakata et al. | |

FOREIGN PATENT DOCUMENTS

| | | |
|---|---|---|
| JP | H03-99000 A | 4/1991 |
| JP | H05-76406 U | 10/1993 |
| JP | 2005-224516 A | 8/2005 |
| JP | 2012-029889 A | 2/2012 |
| JP | 2014-79570 A | 5/2014 |
| JP | 2014-138673 A | 7/2014 |
| JP | 2014-178308 A | 9/2014 |
| JP | 2014-195590 A | 10/2014 |
| JP | 2015-054117 A | 3/2015 |
| JP | 2015-77390 A | 4/2015 |

OTHER PUBLICATIONS

International Search Report dated Sep. 13, 2016, in counterpart International Application No. PCT/JP2016/002887.
Written Opinion of the International Searching Authority dated Sep. 13, 2016, in counterpart International Application No. PCT/JP2016/002887.
International Preliminary Report on Patentability dated Dec. 26, 2017, in counterpart International Application No. PCT/JP2016/002887.
Communication dated Aug. 14, 2018 from the Japanese Patent Office in counterpart Application No. 2017-524618.
Office Action dated Mar. 27, 2020, from the China National Intellectual Property Administration in Application No. 201680036245.7.

* cited by examiner

RADIOGRAPHIC IMAGING APPARATUS

CROSS-REFERENCE TO RELATED APPLICATIONS

This application is a continuation application of International Application No. PCT/JP2016/002887, filed Jun. 15, 2016, the disclosure of which is incorporated herein by reference in its entirety. Further, this application claims priority from Japanese Patent Application No. 2015-124511 filed on Jun. 22, 2015, the disclosure of which is incorporated herein by reference in its entirety.

BACKGROUND

Technical Field

The present invention relates to a radiographic imaging apparatus, and more particularly, to a radiographic imaging apparatus in which a revolvable arm unit supports a radiation source.

Related Art

In the past, a portable radiation-irradiation device, on which only a minimum number of components for radiation irradiation, such as a radiation source and an electrical circuit, are mounted and which can be operated while being held by an operator, has been proposed as disclosed in, for example, JP2012-29889A and "Toshiba Medical Supply Co., Ltd., X-ray equipment IPF-21, [online], [Search on Jul. 30, 1999], Internet URL: http://www.toshiba-iryouyouhin-.co.jp/tmeds/xrays/ipf21.html".

Since this kind of portable radiation-irradiation device is reduced in weight so that an operator can hold and operate the radiation-irradiation device with hands, the radiation-irradiation device is advantageous for the imaging of a subject in various directions.

A cassette where a stimulable phosphor sheet (IP: Imaging Plate) or a silver halide film for an X-ray is received in a housing is generally used in a case in which the radiation image of a subject is to be taken using the above-mentioned portable radiation-irradiation device. That is, in a case in which such a cassette is disposed at a position facing the radiation-irradiation device with a subject interposed therebetween and the radiation-irradiation device is driven in this state, the stimulable phosphor sheet or the like provided in the cassette is irradiated with radiation, such as X-rays, transmitted through the subject and the transmitted radiation image of the subject is recorded on the stimulable phosphor sheet or the like.

In recent years, there have also been many cases in which a so-called electronic cassette to be described later is used instead of the above-mentioned cassette. An example of this electronic cassette is disclosed in JP2014-178308A.

The portable radiation-irradiation device can be held and operated with hands by an operator. However, to prevent shaking and to prevent operator's hands or the like from being exposed to radiation, it is more preferable that the portable radiation-irradiation device is used while being supported by a support device. "Toshiba Medical Supply Co., Ltd., X-ray equipment IPF-21, [online], [Search on Jul. 30, 1999], Internet URL: http://www.toshiba-iryouyouhin-.co.jp/tmeds/xrays/ipf21.html" also discloses an example of such a support device, and particularly, a support device that includes wheel units provided at lower portions of support legs and can travel.

As disclosed in, for example, JP1993-76406U (JP-H05-76406U) and JP1991-99000A (JP-H03-99000A), a radiographic imaging apparatus of which a radiation source mounted on an arm unit is used is also publicly known. In many cases, this kind of radiographic imaging apparatus basically includes a leg unit, a body unit that receives a battery for driving a radiation source and an electrical circuit relating to the drive of the radiation source and is held on the leg unit, an arm unit that is connected to the body unit, and the radiation source that is mounted on the arm unit.

There are also many cases in which the arm unit is divided into two parts, that is, upper and lower arm parts and the upper arm part holding the radiation source is adapted to be revolvable to adjust the height position of the radiation source or to adjust the emission direction of radiation to be emitted from the radiation source.

Since the radiographic imaging apparatus having the above-mentioned basic structure has advantages that the radiographic imaging apparatus can also be easily transported in a narrow place due to mobility and can be used even in an environment where AC power cannot be used, the radiographic imaging apparatus is particularly suitably used to take the radiation image of a patient who is transferred to a medical facility, such as a hospital, or a patient who is lying on a bed in a small hospital room.

The same applies to the radiographic imaging apparatus in which the portable radiation-irradiation device disclosed in the above-mentioned "Toshiba Medical Supply Co., Ltd., X-ray equipment IPF-21, [online], [Search on Jul. 30, 1999], Internet URL: http://www.toshiba-iryouyouhin.co.jp/tmeds/xrays/ipf21.html" and the support device capable of traveling are combined with each other.

However, in a case in which the arm unit is divided into two upper and lower arm parts and the upper arm part is adapted to be revolvable as described above in the radiographic imaging apparatus in the related art in which the arm unit supports the radiation source, it has been confirmed that the radiation source held by the revolving arm part is likely to bump against a subject by mistake.

SUMMARY

A radiographic imaging apparatus according to a first aspect, comprises a leg unit that is capable of traveling on an apparatus-placement surface by a wheel unit, a body unit that is held on the leg unit, an arm unit that is connected to the body unit and is capable of protruding upward from the body unit, and a radiation source that is mounted on the arm unit.

The arm unit includes a body-side part that is capable of extending and retracting in a direction of the protruding of the arm unit and is connected to the body unit and a radiation source-side part on which the radiation source is mounted, the radiation source-side part is connected to a distal end side of the body-side part so as to be revolvable in a direction where an angle between the radiation source-side part and the body-side part changes, and revolution regulating unit configured to allow the radiation source-side part not to revolve in a state in which the body-side part is shorter than a predetermined length is provided.

Here, "upper" and "lower" having been described above mean the upper side and the lower side in a vertical direction in a state in which the radiographic imaging apparatus is in use (a state in which the leg unit is placed on the apparatus-placement surface). Further, the fact that an element protrudes "upward" (toward the upper side) includes not only the fact that an element protrudes vertically upward but also the fact that an element protrudes in a direction having an angle with respect to a vertical direction so as to have a vertically upward component.

Further, "connection" between the body unit and the arm unit may be direct connection or may be indirect connection through other elements.

Furthermore, "the distal end side of the body-side part" means a distal end side in a direction where the arm unit protrudes from the body unit.

In the radiographic imaging apparatus according to a second aspect, the revolution regulating unit is formed of a tubular member of which a proximal end is connected to the body unit and the tubular member is capable of receiving the body-side part and the radiation source-side part of which a longitudinal direction is aligned with a longitudinal direction of the body-side part therein to allow the body-side part and the radiation source-side part to be movable in an axial direction thereof, and the radiation source-side part is set to a length that allows the radiation source-side part to get out of the tubular member in a case in which the body-side part extends to a length equal to or longer than the predetermined length.

The "longitudinal direction" means a direction where the body-side part and the radiation source-side part of the arm unit extend along an arm axis. Even in a case in which the body-side part or the radiation source-side part is formed so as to have an excessively large cross-sectional shape and the size of the body-side part or the radiation source-side part in one direction in this cross section is larger than the length of the body-side part or the radiation source-side part, the meaning of the "longitudinal direction" is the same as described above.

Alternatively, in the radiographic imaging apparatus according to a third aspect, the body-side part of the arm unit includes a tubular outer member of which a proximal end is connected to the body unit and an inner member which is received in the outer member so as to be movable in an axial direction and the radiation source-side part is revolvably connected to a distal end side thereof, and the outer member is capable of receiving the inner member and the radiation source-side part of which a longitudinal direction is aligned with a longitudinal direction of the inner member therein to allow the inner member and the radiation source-side part to be movable in an axial direction thereof, and forms the revolution regulating unit, such that the outer member is set to the same length as the predetermined length.

The "longitudinal direction" means a direction where the inner member and the radiation source-side part of the arm unit extend along an arm axis. Even in a case in which the inner member or the radiation source-side part is formed so as to have an excessively large cross-sectional shape and the size of the inner member or the radiation source-side part in one direction in this cross section is larger than the length of the inner member or the radiation source-side part, the meaning of the "longitudinal direction" is the same as described above.

Further, in the radiographic imaging apparatus according to a fourth aspect, the body-side part of the arm unit is adapted in a state in which the longitudinal direction of the body-side part extends in a direction perpendicular to the apparatus-placement surface.

Furthermore, in the radiographic imaging apparatus according to a fifth aspect, it is preferable that the radiation source-side part is adapted not to revolve until the radiation source-side part is lowered in comparison with a state in which the radiation source-side part is parallel to the apparatus-placement surface.

Moreover, in the radiographic imaging apparatus according to a sixth aspect, the radiation source is adapted to be rotatable about an axis parallel to the longitudinal direction of the radiation source-side part.

Further, in the radiographic imaging apparatus according to a seventh aspect, the radiation source is adapted to be oscillatable in a direction where an elevation angle of a radiation-emission axis is changed, and is provided with oscillating-position fixing unit configured to fix an oscillating position of the radiation source.

Further, in the radiographic imaging apparatus according to an eighth aspect, in a case in which the fixing of the oscillating position of the radiation source performed by the oscillating-position fixing unit is released, the radiation source is adapted to take an oscillating position at which the radiation-emission axis is lowered by an action of its own weight of the radiation source in comparison with a case in which the oscillating position of the radiation source is fixed.

Furthermore, in the radiographic imaging apparatus according to a ninth aspect, the wheel unit is formed of a revolving caster.

Further, in the radiographic imaging apparatus according to a tenth aspect, the body unit is inclined to a state in which an upper end of the body unit is closer to the radiation source than a lower end of the body unit.

Moreover, in the radiographic imaging apparatus according to an eleventh aspect, the wheel unit includes brake unit.

As described above, the radiographic imaging apparatus according to the first aspect is provided with revolution regulating unit for allowing the radiation source-side part of the arm unit not to revolve in a state in which the body-side part of the arm unit is shorter than a predetermined length. Accordingly, in a case in which the body-side part of the arm unit extends to some extent and the radiation source-side part of the arm unit is thus moved up, the radiation source-side part is revolvable. That is, the radiation source-side part is revolvable after the radiation source mounted on the radiation source-side part is moved up to a position that is high to some extent. Accordingly, even though the radiation source-side part revolves, it is difficult for the radiation source, which is present at a high position, to bump against a subject.

DETAILED DESCRIPTION

Figure 1:
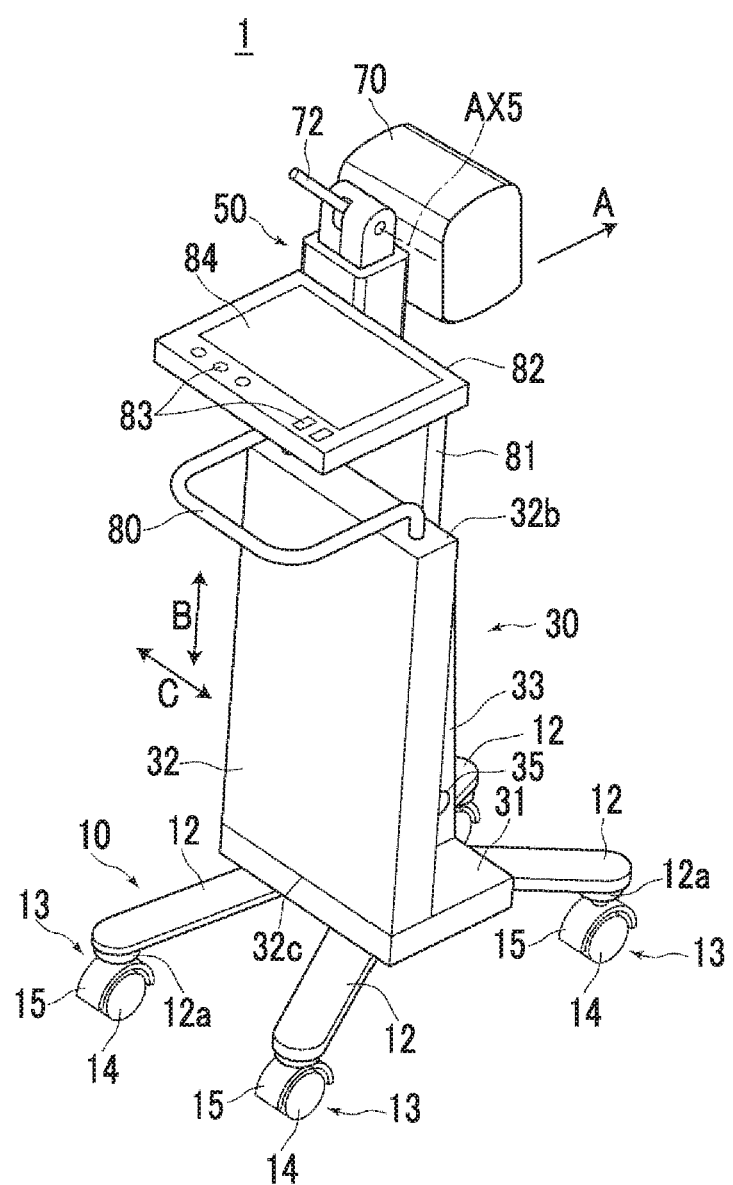
FIG. 1 is a perspective view of a radiographic imaging apparatus according to an embodiment of the invention.
Figure 2:
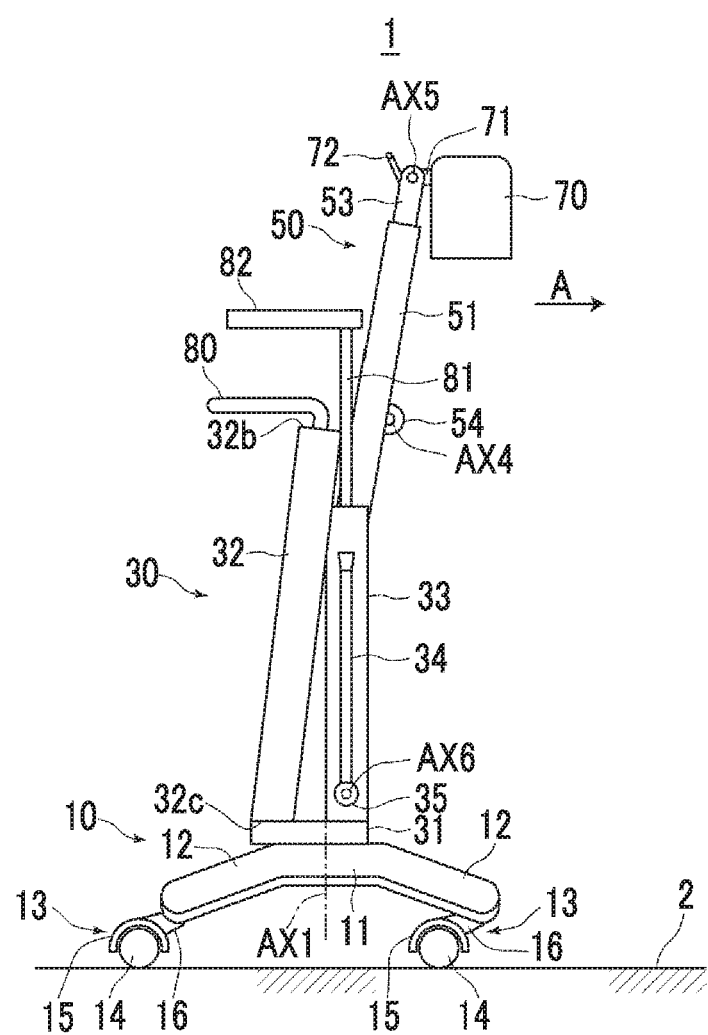
FIG. 2 is a side view showing a state in which the radiographic imaging apparatus of FIG. 1 is not in use.
Figure 3:
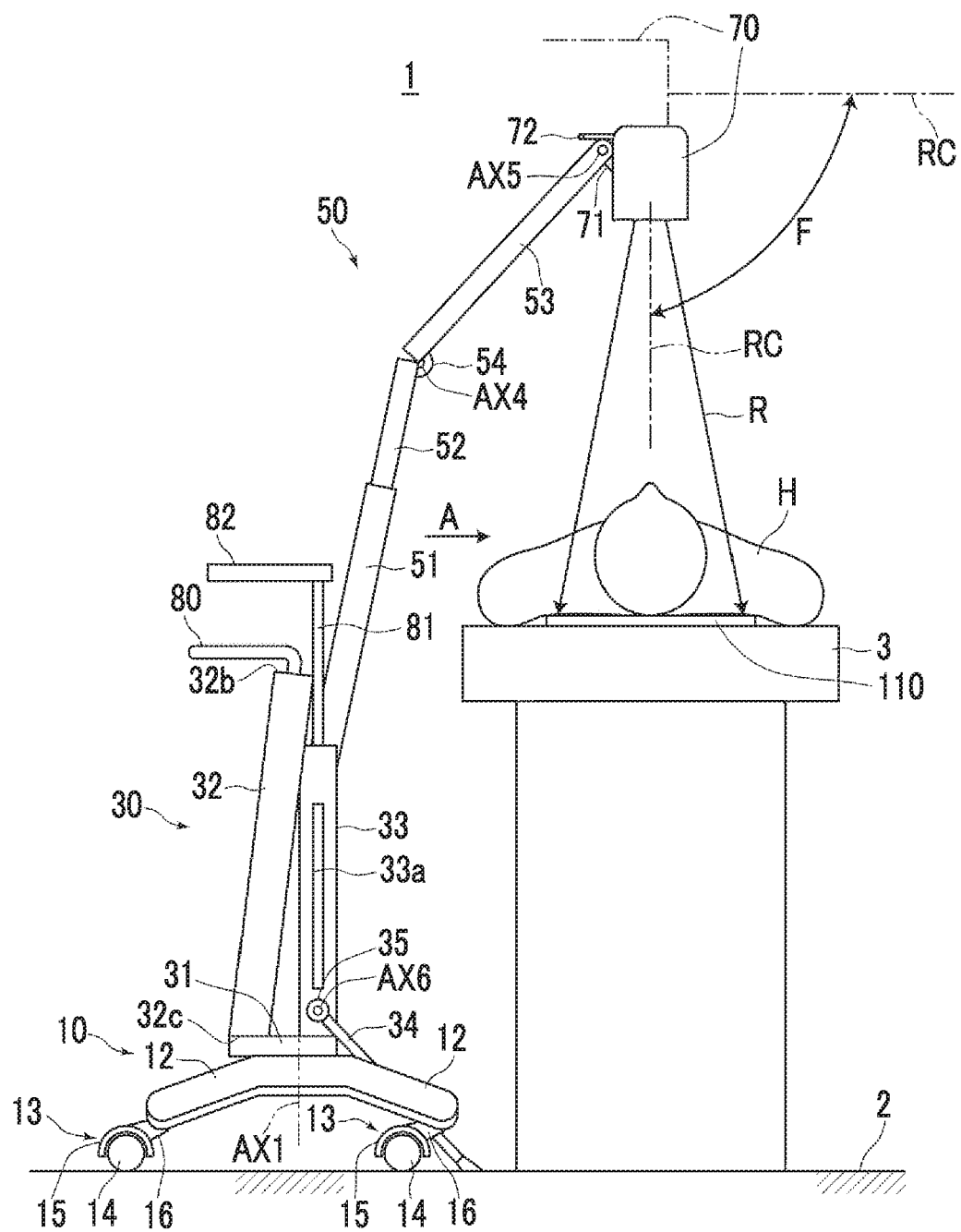
FIG. 3 is a side view showing a state in which the radiographic imaging apparatus of FIG. 1 is in use.
Figure 4:
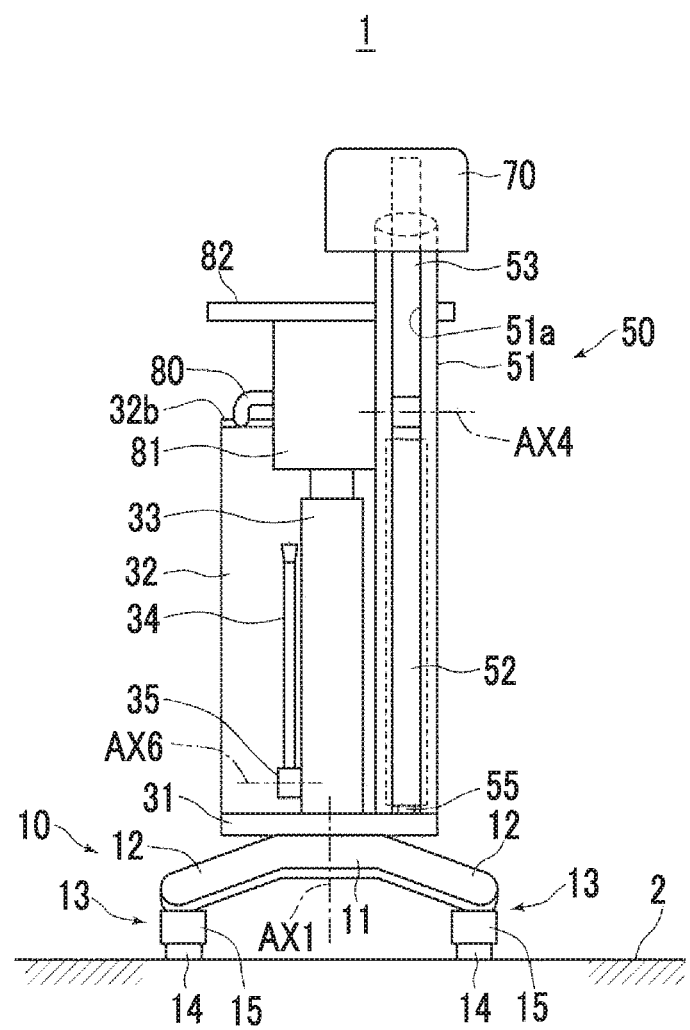
FIG. 4 is a rear view showing a state in which the radiographic imaging apparatus of FIG. 1 is not in use.
Figure 5:
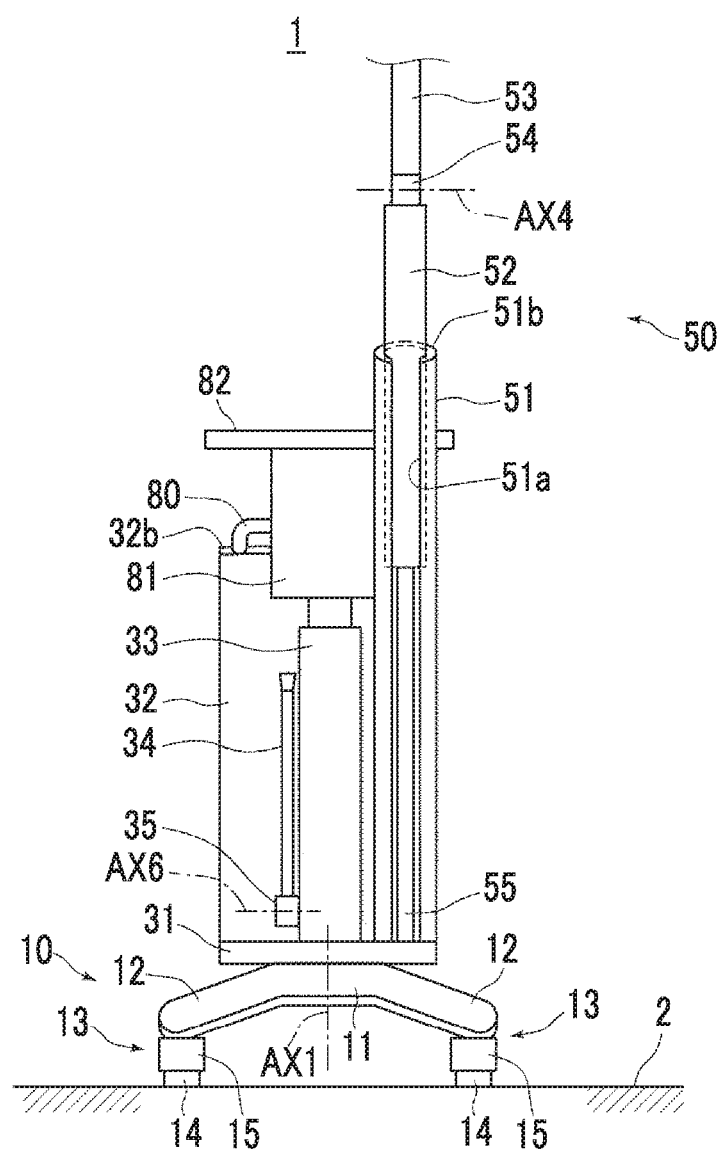
FIG. 5 is a rear view showing a state in which the radiographic imaging apparatus of FIG. 1 is in use.

A radiographic imaging apparatus according to an embodiment of the invention will be described in detail below with reference to the drawings. FIG. 1 is a perspective view showing the shape of the entire radiographic imaging apparatus 1 according to the embodiment of the invention, FIG. 2 is a side view showing a state in which the radiographic imaging apparatus 1 is not in use, FIG. 3 is a side view showing a state in which the radiographic imaging apparatus 1 is in use, FIG. 4 is a rear view showing a state in which the radiographic imaging apparatus 1 is not in use, and FIG. 5 is a rear view showing a state in which the radiographic imaging apparatus 1 is in use.

In the following description, the upper side and the lower side in a vertical direction in a state in which the radiographic imaging apparatus 1 is placed on an apparatus-placement surface 2, such as the floor, of a medical facility are referred to as "upper" and "lower", and a direction perpendicular to the vertical direction in the same state as the state is referred to as a "horizontal" direction.

As shown in FIGS. 1 to 5, the radiographic imaging apparatus 1 of this embodiment includes a leg unit 10 that can travel on an apparatus-placement surface 2, a body unit 30 that is held on the leg unit 10, an arm unit 50 that is connected to the body unit 30, and a radiation source 70 that is mounted on a distal end portion of the arm unit 50. The body unit 30 and the arm unit 50 may be directly connected to each other, or may be indirectly connected to each other through some members.

The body unit 30 has a structure where an element, such as a battery to be described later, is received in a housing 32 fixed onto a base part 31 substantially having the shape of a thick plate. A handle 80, which is used to push or pull the radiographic imaging apparatus 1, is mounted on an upper end of the housing 32. Further, a holding member 33 is fixed onto the base part 31, and a console 82 is held at an upper portion of the holding member 33 through a pedestal 81.

The console 82 includes: input means 83, such as operation buttons and switches, which are used to input signals and the like for instructing the radiographic imaging apparatus 1 to perform various operations; display means 84 that is used to display the state of the radiographic imaging apparatus 1, information input by the input means 83, and the like; and the like. The display means 84 is formed of a so-called touch panel, and signals and the like may be input by a contact operation on the touch panel and the input means 83 may be omitted.

The leg unit 10 includes a horizontal base 11, four legs 12 that extend outward from corner portions of the base 11 by way of example, and wheel units 13 that are mounted on wheel mounting portions 12a provided on lower surfaces of distal end portions of the respective legs 12. The above-mentioned base part 31 is held on the base 11 so as to be rotatable about a rotation axis AX1 extending in the vertical direction. Accordingly, the body unit 30 fixed to the base part 31 and the arm unit 50 to be described later are adapted to be rotatable relative to the leg unit 10 about the rotation axis AX1 in a horizontal plane.

Figure 6:
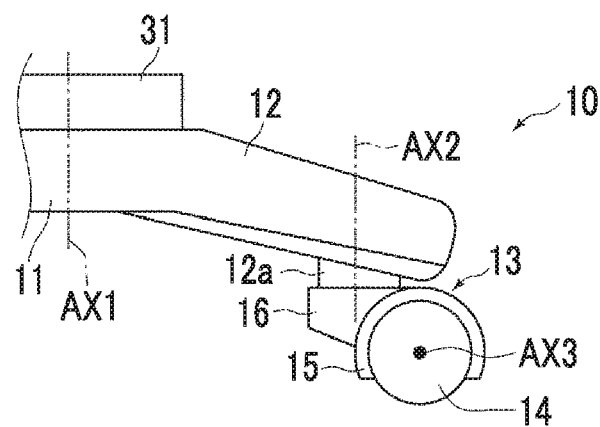
FIG. 6 is a side view of a wheel unit of the radiographic imaging apparatus of FIG. 1.

FIG. 6 is a view showing the side shape of a portion near the wheel unit 13. As shown in FIG. 6, the wheel unit 13 is formed of a so-called revolving caster that can revolve about a revolution axis AX2 extending in the vertical direction. That is, the wheel unit 13 includes a wheel 14 that is formed of, for example, a rubber tire or the like, a wheel holder 15 that holds the wheel 14 to allow the wheel 14 to be rotatable about a horizontal axle AX3, and a revolving part 16 that is integrated with the wheel holder 15; and the revolving part 16 is mounted on the wheel mounting portion 12a of the leg 12 so as to be revolvable about the revolution axis AX2.

The revolution axis AX2 is set to a position that is offset from the axle AX3 in the horizontal plane. Accordingly, in a case in which the leg unit 10 is moved in one horizontal direction, the revolving part 16 revolves so that the revolution axis AX2 is positioned on the front side in this direction and the wheel 14 is positioned on the rear side and the wheel 14 can be freely rotated. Accordingly, in a case in which a worker, such as a radiographer, grips the above-mentioned handle 80 and pushes or pulls the radiographic imaging apparatus 1, the worker can simply and quickly move the radiographic imaging apparatus 1 in an arbitrary direction.

Further, the four wheel units 13 are disposed in this embodiment so that each revolution axis AX2 is positioned at one corner of a common rectangle in a plan view state, that is, a state in which the wheel units 13 are projected onto the apparatus-placement surface 2. Accordingly, the entire leg unit 10 can also be rotated about a vertical line substantially passing through the position of the centroid of the rectangle in the horizontal plane, that is, on the apparatus-placement surface 2. In a case in which the leg unit 10 is rotated as described above, the four wheel units 13 travel while drawing a circular arc so as to follow a common circle.

Casters widely used in, for example, an office chair with casters, a wagon with casters for article transport, a work table with casters, or the like having been publicly known in the past can be appropriately selected and applied as the above-mentioned revolving caster forming the wheel unit 13.

Figure 10:
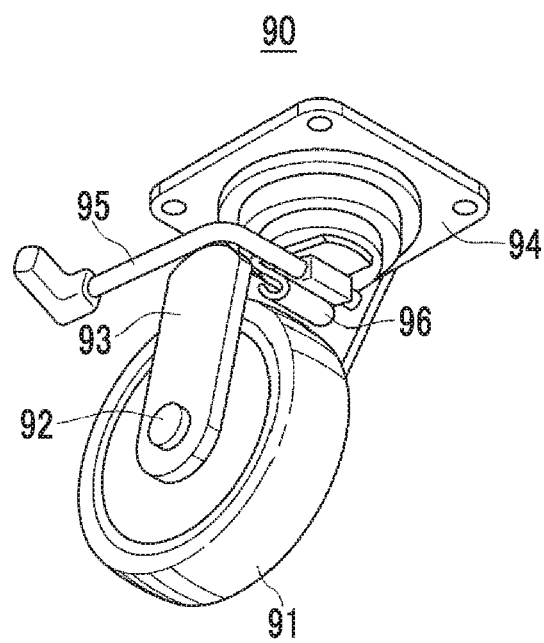
FIG. 10 is a perspective view showing another example of the wheel unit that can be applied to the radiographic imaging apparatus of the invention.
Figure 11:
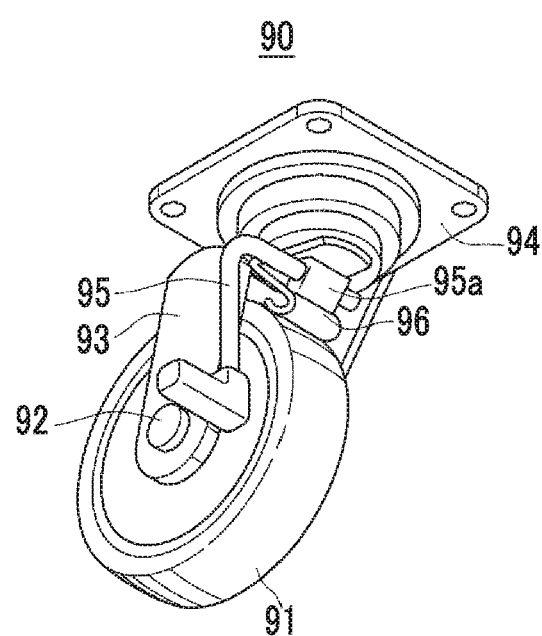
FIG. 11 is a perspective view showing that the wheel unit of FIG. 10 is in another state.

A wheel unit including brake unit may be used instead of the above-mentioned wheel unit 13. FIGS. 10 and 11 are perspective views showing an example of a wheel unit 90 including brake unit, FIG. 10 shows the state of the wheel unit 90 in a case in which a brake is released, and FIG. 11 shows the state of the wheel unit 90 in a case in which a brake is operated.

As shown in FIGS. 10 and 11, the wheel unit 90 includes a wheel 91 that is formed of, for example, a rubber tire or the like, a wheel holder 93 that holds the wheel 91 to allow the wheel 91 to be rotatable about an axle 92, a mounting seat 94 that holds the wheel holder 93 to allow the wheel holder 93 to be revolvable, a crank-shaped brake lever 95 that is held by the wheel holder 93, and a leaf spring 96. The brake lever 95 is held by the wheel holder 93 so as to be rotatable about a shaft thereof close to a proximal end (close to a right end in FIGS. 10 and 11).

In a case in which the brake lever 95 is at a rotational position of FIG. 10, the leaf spring 96 is separated from the wheel 91. Accordingly, the wheel 91 is rotatable. In a case in which the brake lever 95 is rotated from this state and is moved to a rotational position of FIG. 11, a protruding portion 95a formed on the shaft of the brake lever 95 close to the proximal end pushes the leaf spring 96 so that the leaf spring 96 is in pressure contact with the peripheral surface of the wheel 91. Accordingly, the wheel 91 cannot be rotated and the wheel 91 is in a braking state.

In a case in which the wheel units 90 including the above-mentioned brake unit are applied to the leg unit 10 and the wheels 91 are braked after the leg unit 10 is made to travel to move the radiographic imaging apparatus 1 to a predetermined position, the careless movement of the radiographic imaging apparatus 1 can be prevented.

Further, a revolving caster that includes brake unit for preventing a revolving part from revolving about a revolution axis (AX2 in the case of an example of FIG. 6) is also provided as the revolving caster. In a case in which such a revolving caster is applied, the careless movement of the radiographic imaging apparatus 1 caused by the revolution of each revolving part can be prevented while the rotation of each wheel is allowed. The wheel unit including that kind of brake unit can also be applied to the invention, and a wheel unit, which can brake both the rotation of the wheel and the revolution of the revolving part, can also be applied to the invention.

Furthermore, for example, a button or a lever, which is installed near the handle 80, other than the above-mentioned brake lever 95 may be operated to brake the wheel unit 13. Further, the wheel unit 13 may be adapted to be automatically braked in a case in which the moving speed of the wheel unit 13 is detected and the detected moving speed exceeds a certain set speed. Furthermore, in a case in which the detected moving speed exceeds the certain set speed, an alert using warning sound, the flicker of a lamp, or the like may be generated to alert a user of the apparatus. Only such an alert may be generated, and the wheel unit 13 may be braked together with the generation of the alert.

In addition, the wheel unit 13 may be adapted to be automatically braked in a case in which the separation of the hands of a user of the apparatus from the handle 80 is detected. Further, to prevent the fall of the radiographic imaging apparatus 1 in a case in which the wheel unit 13 is automatically braked as described above, it is preferable that the wheel unit 13 is adapted to be completely braked after the speed of the wheel unit 13 is gradually reduced. Further, in a case in which the wheel unit 13 is automatically braked, it is preferable that the four wheel units 13 are simultaneously braked.

Furthermore, the radiographic imaging apparatus 1 may be adapted to automatically brake and lock the wheel units 13 so as to eventually prevent the radiation source 70 from moving in a case in which a radiation image is taken. In this case, it is preferable that the radiographic imaging apparatus 1 is adapted to detect a certain operation immediately before the drive of the radiation source 70 and to automatically brake the wheel units 13 in a case in which the certain operation is detected. Examples of the above-mentioned operation include a release operation of a camera that takes an optical image used to check a radiation-irradiation range.

Figure 7:
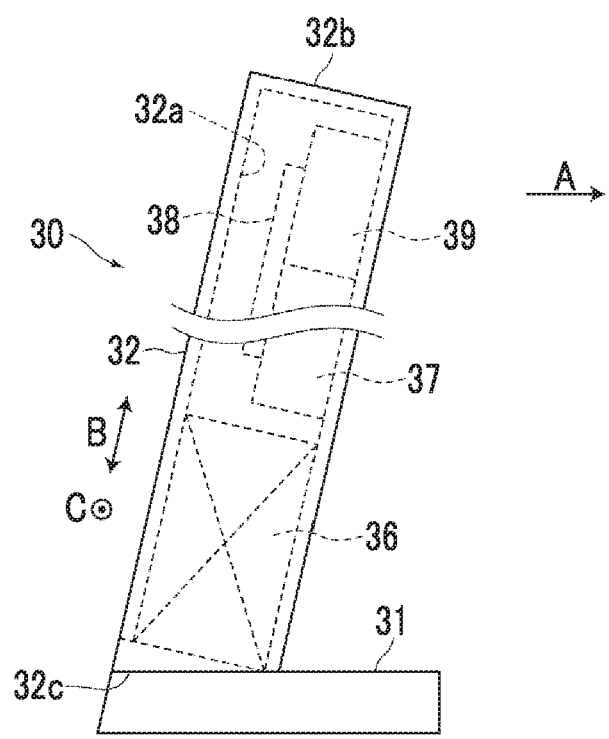
FIG. 7 is a side view of a body unit, which is partially broken, of the radiographic imaging apparatus of FIG. 1.
Figure 8:
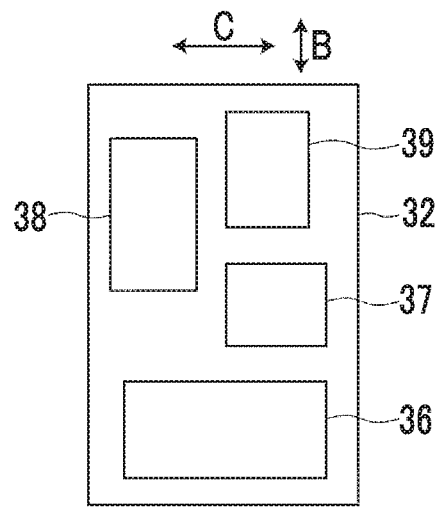
FIG. 8 is a schematic diagram showing a state in which a plurality of circuits are disposed in the body unit of FIG. 7.

Next, the body unit 30 will be described in detail with reference to FIGS. 7 and 8. FIG. 7 is a side view of the body unit 30 that is partially broken. As clearly shown in FIGS. 1 and 7, the housing 32 of the body unit 30 is formed substantially in the shape of a thin rectangular parallelepiped, and an opening (not shown) is provided on the front surface of the housing 32, that is, the surface of the housing 32 from which the handle 80 protrudes, and the opening is closed by a lid 32a.

In this embodiment, the housing 32 of the body unit 30 is fixed to the base part 31 in a state in which the housing 32 is inclined so that an upper end 32b is closer to the radiation source 70 than a lower end 32c. Arrow A shown in FIG. 7 corresponds to arrow A of FIG. 1, and the radiation source 70 is positioned on the front side of the housing 32 in the direction of arrow A in FIG. 7. The housing 32 may be formed separately from the base part 31 and may then be fixed to the base part 31, or may also be formed integrally with the base part 31 from the beginning.

A DC power supply circuit 37, a drive control circuit 38, and an inverter (DC-AC conversion circuit) 39 are received in the housing 32 in addition to a battery 36 for driving the radiation source 70. These circuits 37 to 39, which are divided into blocks, are publicly known circuits that relate to the drive of the radiation source 70, and examples of these are disclosed in JP2000-127834A. The replacement, maintenance and inspection, repair, and the like of the battery 36 and the circuits 37 to 39 can be performed through the opening in a state in which the lid 32a is opened.

As clearly shown in FIGS. 2 and 3, the arm unit 50 protrudes from the body unit 30 in one horizontal direction (the direction of arrow A), but all the circuits 37 to 39, which are divided into blocks, are arranged in directions crossing the direction of arrow A. In more detail, as in the schematic arrangement state shown in FIG. 8, the circuits 37 to 39 are arranged in the direction of arrow B crossing the direction of arrow A and in the direction of arrow C crossing the direction of arrow A. The direction of arrow B and the direction of arrow C are the longitudinal direction and the lateral direction of the housing 32 formed substantially in the shape of a thin rectangular parallelepiped. Since the circuits 37 to 39 are arranged in these directions, the housing 32, that is, the body unit 30 can be formed to be thinner. Further, since the battery 36 is also particularly arranged in the direction of arrow B together with the circuits 37 to 39 in this embodiment, this arrangement is more advantageous for the formation of the thin body unit 30.

Figure 9:
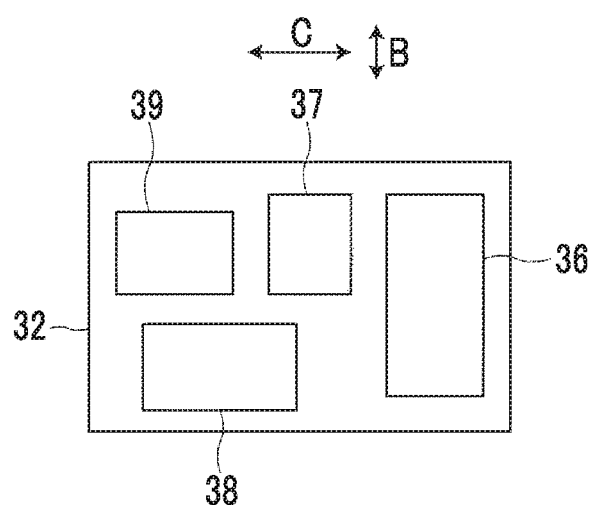
FIG. 9 is a schematic diagram showing another example of the state in which the plurality of circuits are disposed in the body unit.

In this embodiment, the housing 32 is formed in a shape where a length in the longitudinal direction is longer than a length in the lateral direction. However, as in the schematic shape shown in FIG. 9, the housing 32 may also be formed in a shape where a length in the longitudinal direction is shorter than a length in the lateral direction. Since the battery 36 and the circuits 37 to 39 are arranged in directions crossing the direction of arrow A even in this case, the body unit 30 can be formed to be thin. In a case in which the housing 32 is formed to be significantly long in the longitudinal direction or to be significantly long in the lateral direction, the battery 36 and the circuits 37 to 39 may be arranged only in the direction of arrow B or only in the direction of arrow C.

As clearly shown in FIGS. 2 and 3, a base portion 35 of a rod-like auxiliary leg 34 is mounted on the side surface of the holding member 33 so that the rod-like auxiliary leg 34 is rotatable about a rotation axis AX6. Further, as clearly shown in FIG. 3, the holding member 33 is provided with a slit 33a extending inward from the side surface of the holding member 33. For example, an electronic cassette or the like to be described later can be received in the slit 33a.

Here, a size relationship between the leg unit 10 and the body unit 30 will be described with reference to FIG. 12. As described above, the four wheel units 13 of the leg unit 10 are revolvable on the apparatus-placement surface 2 so as to follow a common circle. The radiographic imaging apparatus 1 is revolvable by the leg unit 10 to change the traveling direction thereof or to allow the radiation source 70 to face a desired direction, but the above-mentioned revolution is the revolution in the "smallest" radius. That is, the revolution of the leg unit 10, which revolves about a vertical line not present inside the four wheel units 13 in a plan view state so that the four wheel units 13 follow circles different from each other, is the revolution in a large radius. The above-mentioned revolution in the "smallest" radius correspond to a case in which the leg unit 10 revolves so that at least two wheel units 13 follow a common circle.

Figure 12:
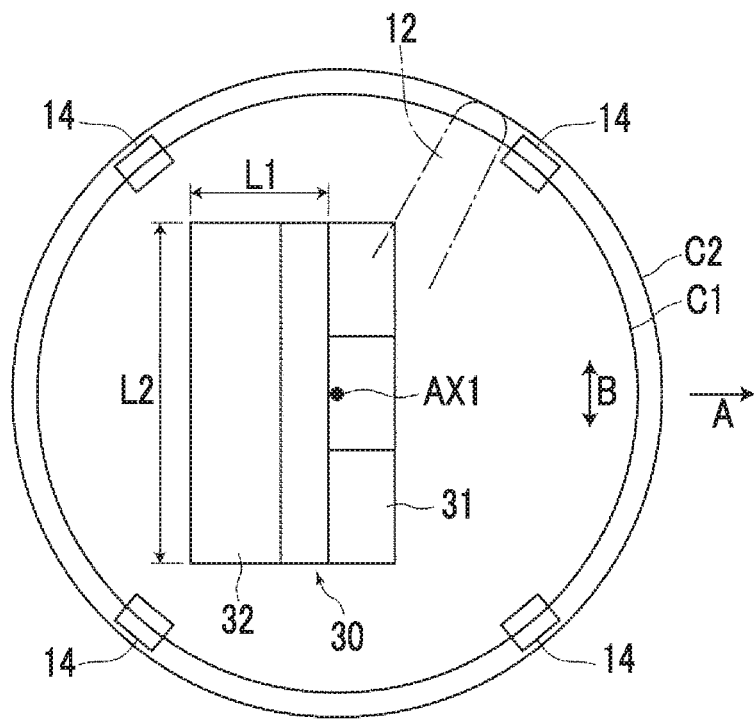
FIG. 12 is a diagram illustrating a size relationship between the body unit and a leg unit of the radiographic imaging apparatus of FIG. 1.

In FIG. 12, a common circle where the four wheel units 13 follow in a case in which the leg unit 10 revolves in the smallest radius is denoted by C1 and a circular locus drawn by the outermost end of the leg 12 (that is, the outermost end of the leg unit 10) in this case is denoted by C2. Further, FIG. 12 shows a state in which the body unit 30 and the base part 31 provided on the leg unit 10 are shown in plan view. As shown in FIG. 12, the body unit 30 is present inside the circular locus C2 drawn by the outermost end of the leg unit 10. Likewise, the base part 31 is also present inside the circular locus C2.

According to the above-mentioned structure, if the user of the apparatus pays attention so that the outermost end of the leg 12 does not bump against anything in a case in which the user of the apparatus revolves the radiographic imaging apparatus 1 in the smallest radius to change the direction of the radiation source 70, the user of the apparatus can avoid the bump of the body unit 30 or the base part 31 against something.

Further, as shown in FIG. 12, the body unit 30 is formed in a shape where the length L1 of the body unit 30 in a direction (the direction of arrow A) in which the arm unit 50 protrudes from the body unit 30 is shorter than the length L2 of the body unit 30 in a direction (the direction of arrow B) perpendicular to the direction in a state in which the body unit 30 is shown in plan view. Since the body unit 30 is formed such a shape, the radiographic imaging apparatus 1 can be formed in a slim shape that does not occupy a wide place in a case in which the arm unit 50 is most reduced in length and is received in a tubular member 51 as described later. It is preferable that the length L1 is generally shorter than ⅓ of the length of the length L2.

The body unit 30 has been adapted to be rotatable relative to the leg unit 10 about the rotation axis AX1 as described above, but it is preferable that the body unit 30 is provided with lock means for preventing the rotation of the body unit 30. A component having a structure, which simultaneously locks the rotation of the body unit 30 in a case in which the component brakes the wheel unit 13 while interlocking with brake operating means (for example, the brake lever 95 of FIG. 10, or the like) for braking the wheel unit 13, is preferable as the lock means. Alternatively, a component having a structure, which locks the rotation of the body unit 30 by an independent operation, may be used as the lock means. If that kind of lock means is provided, the rotation of the body unit 30 caused at the time of rotation of the radiation source 70 can be prevented in a case in which the radiation source 70 is adapted to be rotatable relative to the arm unit 50 about a rotation axis AX9 (see FIG. 16) as described later.

Returning to FIGS. 1 to 5, the arm unit 50 will be described in detail below. The arm unit 50 includes a tubular member 51 that has a substantially "C"-shaped cross-sectional shape formed by a slit 51a extending in an axial direction and provided at a part of a substantially cylindrical member, a body-side arm 52 (a body-side part of the arm unit) that can be received in the tubular member 51 so as to be movable in the axial direction, and a radiation source-side arm (a radiation source-side part of the arm unit) 53 that can be received in the tubular member 51 so as to be movable in the axial direction likewise. The tubular member 51 is fixed onto the base part 31 in a state in which the tubular member 51 is inclined in substantially the same direction as the housing 32 inclined as described above. The tubular member 51 may be formed of a cylindrical member or a rectangular cylindrical member other than the member having a substantially "C"-shaped cross-sectional shape as described above, and may be formed of half-split members having a cross-sectional shape in which two circular arcs face each other.

A lower end portion of the radiation source-side arm 53 is connected to an upper end portion of the body-side arm 52 through a revolution-holding mechanism 54 so as to be revolvable about a revolution axis AX4. The revolution axis AX4 is an axis extending in the horizontal direction. The radiation source-side arm 53 revolves about the revolution axis AX4 in a direction where an angle between the radiation source-side arm 53 and the body-side arm 52 changes. The revolution-holding mechanism 54 holds both the radiation source-side arm 53 and the body-side arm 52 so that the radiation source-side arm 53 revolves with respect to the body-side arm 52 through a friction mechanism. Accordingly, the radiation source-side arm 53 can revolve in a case in which an external force, which is strong to some extent, is applied to the radiation source-side arm 53, and the radiation source-side arm 53 maintains an angle relative to the body-side arm 52 without revolving as long as an external force is not applied.

The body-side arm 52 includes a cylinder (not shown) forming a gas spring built therein, and forms the body-side part of the arm unit together with a piston rod 55 combined with the cylinder. The gas spring basically includes the cylinder that is filled with gas, a piston that partitions the inside of the cylinder into an upper chamber and a lower chamber, a communication passage that allows these upper and lower chambers to communicate with each other, an on-off valve that opens and closes the communication passage, an operation lever that operates the on-off valve, and the piston rod 55 of which an upper end is connected to the piston.

In the past, the gas spring having the above-mentioned structure has been widely applied as a height adjustment mechanism in a chair of which the height of a seating surface can be changed, or the like. In this embodiment, the body-side part (including the body-side arm 52 and the piston rod 55) of the arm unit are adapted to be capable of extending and retracting so that the length of the arm unit 50 can be adjusted. This will be described in detail below.

In a case in which, for example, the operation lever is pulled to keep the on-off valve in an open state, the upper and lower chambers communicate with each other and gas can flow between the upper and lower chambers. Accordingly, the cylinder, that is, the body-side arm 52 is movable relative to the piston rod 55. Therefore, in a case in which a force, which is large to some extent, is applied to push the body-side arm 52 down in the tubular member 51, the entire body-side arm 52 is received in the tubular member 51 as shown in FIG. 4. In this case, a part of the radiation source-side arm 53 is also received in the tubular member 51 in a state in which the longitudinal direction of the radiation source-side arm 53 is aligned with the longitudinal direction of the body-side arm 52. In a case in which the body-side arm 52 and the radiation source-side arm 53 are received in the tubular member 51 in this way, the revolution-holding mechanism 54 is moved in the slit 51a of the tubular member 51.

In a case in which the radiographic imaging apparatus 1 is not in use, the arm unit 50 is in a state shown in FIG. 4. Since a part of the radiation source-side arm 53 is positioned in the tubular member 51 in this state, the radiation source-side arm 53 cannot revolve about the revolution axis AX4. That is, in this embodiment, the tubular member 51 functions as revolution regulating unit for allowing the radiation source-side arm 53 not to revolve in a state in which the body-side part of the arm unit 50 is shorter than a predetermined length. The "predetermined length" in this case is the length of the body-side part of the arm unit 50 (the total length of the body-side arm 52 and a portion of the piston rod 55 protruding from the body-side arm 52) that allows the lower end of the radiation source-side arm 53 to slightly get out of the tubular member 51.

In a case in which the operation lever is released after the arm unit 50 is in the state shown in FIG. 4, the on-off valve is in a closed state and the flow of gas is regulated. Accordingly, the state of the arm unit 50 is kept. After that, in a case in which the operation lever is operated so that the on-off valve is in the open state, the body-side arm 52 is movable relative to the piston rod 55 as described above and the body-side arm 52 is moved up in the tubular member 51 by the repulsive force of gas compressed in the upper chamber. In this case, the body-side arm 52 can be moved up to a position at which the upper end of the body-side arm 52 protrudes from the tubular member 51 as shown in FIG. 3. Since the entire radiation source-side arm 53 also gets out of the tubular member 51 in this state, the radiation source-side arm 53 is revolvable about the revolution axis AX4.

If the operation lever is released and the on-off valve in the closed state in a case in which the on-off valve is in the open state as described above and the body-side arm 52 is moved up in the tubular member 51, the flow of gas is regulated and the body-side arm 52 is stopped at a position at that time. In this way, the length of a portion of the body-side arm 52, which protrudes from the tubular member 51, that is, the entire length of the arm unit 50 can be adjusted.

The radiation source 70 has a structure where, for example, an X-ray tube, a booster circuit, a cooling means for cooling the X-ray tube, and the like are received in a housing. Further, the radiation source 70 is mounted on the distal end portion of the above-mentioned radiation source-side arm 53 through a support member 71 so as to be capable of oscillating about an oscillation axis AX5. The oscillation of the radiation source 70 is oscillation in a direction where an elevation angle of a radiation-emission axis RC is changed as shown in FIG. 3 by an arrow F. Since the direction of the radiation-emission axis RC is changed in a case in which the radiation source 70 can oscillate in this way, the radiation images of subjects, which are in various positions, can be taken.

The oscillating position of the radiation source 70, which is adapted to be capable of oscillating, is adapted to be capable of being fixed by the operation of a lock lever 72. Further, in a case in which the fixing of the oscillating position performed by the lock lever 72 is released, the radiation source 70 is adapted to take an oscillating position at which the radiation-emission axis RC is lowered by the action of its own weight of the radiation source 70 in comparison with a case in which the oscillating position of the radiation source 70 is fixed. The oscillating position at which the radiation-emission axis RC is lowered is most preferably an oscillating position at which the radiation-emission axis RC is directed downward in the vertical direction. According to the above-mentioned structure, after the taking of the radiation image of, for example, a subject ends and the radiographic imaging apparatus 1 is moved in the lateral direction so as to be separated from the subject, it is possible to prevent the subject from being irradiated with radiation by mistake.

Next, the taking of a radiation image performed by the radiographic imaging apparatus 1 having the above-mentioned structure will be described. In the state which is shown in FIG. 2 and in which the radiographic imaging apparatus 1 is in not in use, the radiographic imaging apparatus 1 is transported to a use position while the radiographic imaging apparatus 1 is made to travel on the apparatus-placement surface 2, such as the floor, of a hospital by the wheel units 13 of the leg unit 10. In this case, since the wheel units 13 are formed of the above-mentioned revolving casters, the radiographic imaging apparatus 1 can be moved in a front-back direction and the lateral direction, and can also be moved along a large curve, and can also revolve at that position. Accordingly, the radiographic imaging apparatus 1 can be quickly transported to a use position in a state in which the radiographic imaging apparatus 1 revolves in a small radius.

The taking of a radiation image is performed on a subject H who is supine on a supine table 3, such as a bed, as shown in, for example, FIG. 3. In a case in which the radiographic imaging apparatus 1 is set at an imaging position shown in FIG. 3, the radiographic imaging apparatus 1 can also be moved in the height direction of a subject H, that is, in the form of so-called the side-crawl by the wheel units 13 formed of revolving casters. Accordingly, the radiographic imaging apparatus 1 can be easily set to the optimum position.

In this case, since the body unit 30 is formed in a thin shape as a whole as described above and the holding member 33 is also formed in a thin shape, the radiographic imaging apparatus 1 can also easily enter, for example, a narrow space between beds. Further, since the body unit 30 and the holding member 33 are formed in a thin shape as a whole, the radiographic imaging apparatus 1 can also be set to a position very close to the bed while the leg unit 10 is inserted into a space under the bed. Accordingly, since the adjustment of the position of the radiation source 70, which is caused by the extension, the retraction, and the revolution of the arm unit 50, may be less performed, time required to take an image can be shortened.

After the radiographic imaging apparatus 1 is set to the optimum position, the body-side arm 52 of the arm unit 50 extends to an arbitrary position where the body-side arm 52 protrudes from the tubular member 51 as described above. After that, the radiation source-side arm 53 of the arm unit 50 is made to revolve about the revolution axis AX4 so that the radiation source 70 is set to the optimum position, and the radiation source 70 is made to oscillate about the oscillation axis AX5 so that the radiation-emission axis RC is set to the optimum direction.

Furthermore, since the base part 31 holding the arm unit 50 is adapted to be rotatable on the leg unit 10 about the rotation axis AX1 in this embodiment, the direction of the arm unit 50 can also be changed by the rotation of the base part 31 to adjust the position and direction of the radiation source 70.

Since the radiation source-side arm 53 of the arm unit 50 cannot revolve due to the action of the tubular member 51 as described above in a case in which the body-side arm 52 does not extend to a position where the body-side arm 52 protrudes from the tubular member 51, it is possible to prevent a problem that the radiation source-side arm 53 revolves and the radiation source 70 bumps against a subject H in a state in which the radiation source 70 is at a relatively low position. Further, since the arm unit 50 protrudes in a direction (the direction of arrow A) where the arm unit 50 is closer to the subject H than the body unit 30, the radiation source 70 can be disposed so as to face the subject H who is present at a position distant from the body unit 30.

In this case, the rod-like auxiliary leg 34 is rotated about the rotation axis AX6 to be in a state in which the distal end of the rod-like auxiliary leg 34 is in contact with the apparatus-placement surface 2 as shown in FIG. 3. For example, a member hard to slip, such as rubber, is mounted on the distal end of the auxiliary leg 34 to prevent slip. The auxiliary leg 34 in this state functions as a so-called "tension rod", and prevents the radiographic imaging apparatus 1 from falling down toward the distal end of the radiation source-side arm 53 by which the heavy radiation source 70 is held. For example, a member having the shape of an outrigger for preventing the fall of a crane truck is received in the holding member 33 instead of the above-mentioned auxiliary leg 34, and may be pulled in the direction of arrow A and be used in a case in which a radiation image is to be taken.

For example, an electronic cassette 110 to be described later is disposed under the subject H and the electronic cassette 110 is irradiated with radiation (for example, X-rays) R emitted from the radiation source 70 through the subject H, so that the taking of a radiation image in this example is performed. A command, which drives the radiation source 70, or the like is made by the console 82. Further, a cassette where a stimulable phosphor sheet (IP: Imaging Plate) or a silver halide film for an X-ray publicly known in the related art is received in a housing may be used instead of the electronic cassette 110.

Figure 14:
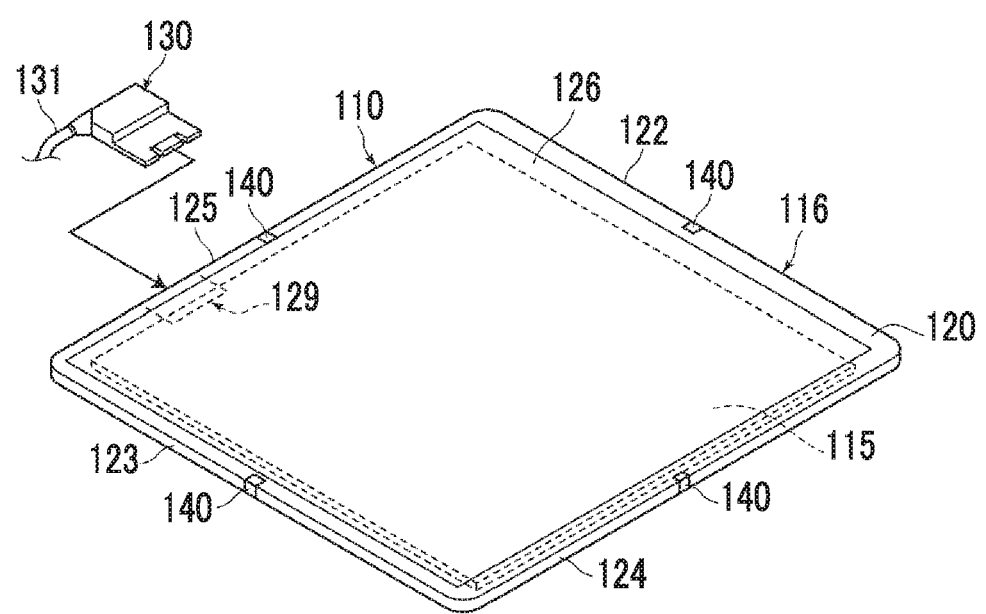
FIG. 14 is a perspective view showing the front side of an electronic cassette.
Figure 15:
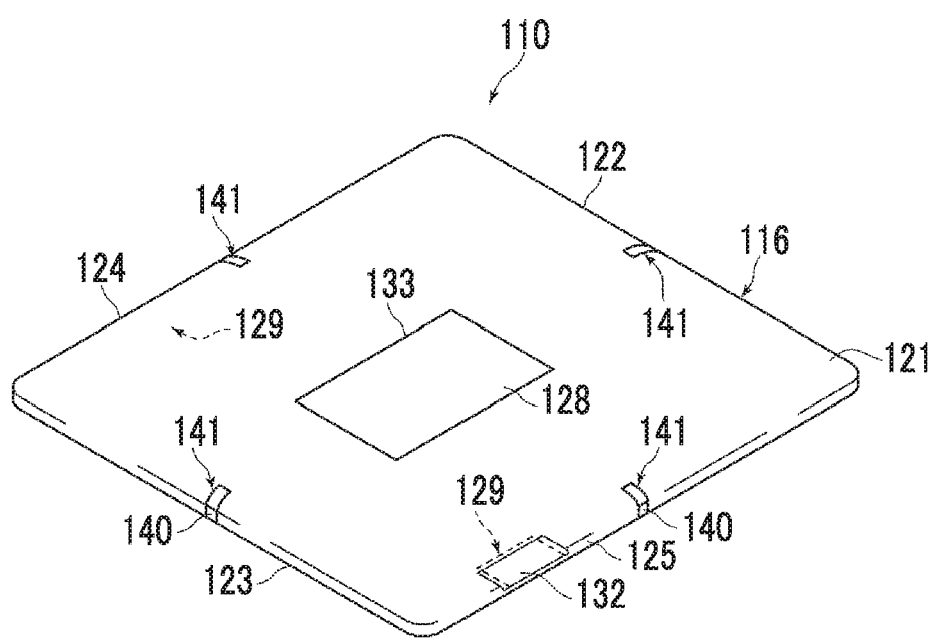
FIG. 15 is a perspective view showing the back side of the electronic cassette.

The electronic cassette 110 will be simply described here with reference to FIGS. 14 and 15. FIGS. 14 and 15 show the appearance of the electronic cassette 110 from the front side and the back side, respectively. The electronic cassette 110 of this example is used for, for example, medical radiography, and includes an image detection unit 115 that detects a transmitted X-ray image of the subject H on the basis of X-rays having been transmitted through the subject and a portable housing 116 that receives the image detection unit 115.

As well known, the image detection unit 115 includes a scintillator (phosphor) that converts incident X-rays into visible light and a thin-film-transistor (TFT) active matrix substrate. A rectangular imaging region in which a plurality of pixels for accumulating electric charges corresponding to visible light emitted from the scintillator are arranged is formed on the TFT active matrix substrate. A gate driver that applies gate pulses to a gate of a TFT to switch the TFT, a signal processing circuit that converts the electric charges accumulated in the pixels into voltage signals representing an X-ray image and outputs the voltage signals, a control unit that controls the drive of the gate driver and the signal processing circuit, and the like are built in the housing 116 in addition to the image detection unit 115.

The housing 116 has the shape of a rectangular parallelepiped including a front surface 120 on which X-rays are incident, a back surface 121 that faces the front surface 120, and four side surfaces 122, 123, 124, and 125. The housing 116 is made of, for example, a conductive resin and also functions as an electromagnetic shield that prevents the penetration of electromagnetic noise into the electronic cassette 110 and the emission of electromagnetic noise from the electronic cassette 110 to the outside. The housing 116 has substantially the same size as, for example, a film cassette or an imaging plate (IP) cassette and a computed radiography (CR) cassette that is based on International Organization for Standardization (ISO) 4090:2001.

A rectangular opening is formed on the front surface 120, and a transmissive plate 126 is mounted on the opening. A protective film (not shown) made of a resin, which transmits X-rays, is attached to the surface of the transmissive plate 126. Accordingly, the front surface 120 is a flat surface. The transmissive plate 126 has a planar size slightly larger than the planar size of the imaging region, and is made of a carbon material that is light and has a high stiffness and a high X-ray transmissivity.

The electronic cassette 110 includes a control device that controls the operation of the electronic cassette 110 and an antenna and an oscillation circuit that generate radio waves for the wireless communication of various kinds of information, such as X-ray images. In a case in which this wireless communication function is used, the electronic cassette 110 is driven by power to be supplied from a battery 128 and can be used in a so-called cableless form.

Further, the electronic cassette 110 includes a female connector 129 that communicates with a control device (not shown) by wire. A male connector 130 is connected to the female connector 129. One end of a cable 131, which is used for the wired connection between the electronic cassette 110 and the control device, is connected to the male connector 130. The other end of the cable 131 is connected to a connector (not shown) that is to be connected to the control device. The female connector 129 is covered and protected with a lid 132 in a case in which the male connector 130 is not connected, such as a case in which the wireless communication function is used, and the like.

The electronic cassette 110 receives not only various kinds of information supplied from the control device but also supplied power through the female connector 129. In a case in which the female connector 129 and the male connector 130 are connected to each other, the electronic cassette 110 is driven by power to be supplied from the control device. Furthermore, the battery 128 can also be charged with power to be supplied from the control device.

A battery-mounting portion 133 is provided at the central portion of the back surface 121. The battery 128, which supplies power used to drive the electronic cassette 110, is detachably mounted in the battery-mounting portion 133. FIG. 15 shows a state in which the battery 128 is mounted in the battery-mounting portion 133.

The battery-mounting portion 133 is a recess that is recessed toward the front surface 120 from the back surface 121. The battery-mounting portion 133 is formed to have the same shape and size as the planar shape and the planar size of the battery 128 so that the battery 128 is received substantially without a gap. The depth of the battery-mounting portion 133 from the back surface 121 is also substantially the same as the thickness of the battery 128. For this reason, in a state shown in FIG. 15 in which the battery 128 is mounted in the battery-mounting portion 133, the upper surface of the battery 128 is exposed from the back surface 121 and the upper surface of the battery 128 and the back surface 121 are flush with each other.

The electronic cassette 110 is provided with four marks 140 and four indicators 141 that are formed of, for example, light-emitting elements, such as LEDs or organic electroluminescence (EL) elements. These marks 140 and these indicators 141 function to inform an operator of the position of the middle of each of sides of the rectangular imaging region.

After X-ray image information is recorded in the electronic cassette 110, the electronic cassette 110 is connected to an image recording device or an image display device for receiving voltage signals representing an X-ray image and the transmitted X-ray image of a subject H is recorded or reproduced and displayed on the basis of the signals.

Figure 13:
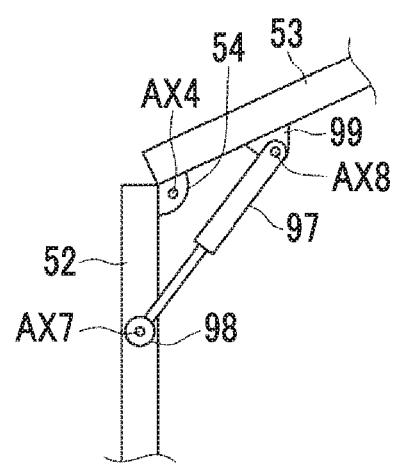
FIG. 13 is a side view showing another example of an arm unit that can be applied to the radiographic imaging apparatus of the invention.

Here, it is preferable that it is the body-side arm 52 and the radiation source-side arm 53 of the arm unit 50 shown in FIG. 3 and the like are connected to each other by a gas spring 97 as shown in FIG. 13 so that the radiation source-side arm 53 is not lowered than a state in which the radiation source-side arm 53 is horizontal. Accordingly, in a case in which the radiation source 70 (see FIG. 3) held at the distal end portion of the radiation source-side arm 53 is disposed above the subject H and images the subject H, it is possible to avoid a situation that the radiation source-side arm 53 is carelessly lowered and the radiation source 70 bumps against the subject H.

The same elements of in FIG. 13 as the elements shown in FIGS. 1 to 12 having been previously described will be denoted by the same reference numerals as the reference numerals of FIGS. 1 to 12, and the description thereof will be omitted as long as the description thereof is not particularly needed (the same applies hereinafter). In the structure shown in FIG. 13, in detail, one end and the other end of a gas spring 97 are held at a holding portion 98 fixed to the body-side arm 52 and a holding portion 99 fixed to the radiation source-side arm 53 so as to be rotatable about rotation axes AX7 and AX8, respectively. In a case in which the body-side arm 52 and the radiation source-side arm 53 are to be received in the tubular member 51 shown in FIGS. 3 and 4, and the like, the holding portions 98 and 99 protruding from the respective arms 52 and 53 are positioned in the slit 51a of the tubular member 51. Accordingly, even though these protruding holding portions 98 and 99 are provided, the arms 52 and 53 can be received in the tubular member 51.

Next, another example of the arm unit will be described with reference to FIG. 16. A body-side part of an arm unit 200 shown in FIG. 16 includes a tubular outer member 61 of which a proximal end is connected to, for example, the body unit 30 (see FIG. 2 and the like) and an inner member 62 which is received in the outer member 61 so as to be movable in an axial direction and a radiation source-side arm 63 is revolvably connected to a distal end side thereof. The radiation source-side arm 63 is connected to the inner member 62 through a connecting portion 64 so as to be revolvable about a revolution axis AX4. Further, the tubular outer member 61 is formed in, for example, a rectangular cylindrical shape.

The inner member 62 is received in the outer member 61 through an appropriate friction mechanism or through the above-mentioned gas spring. Accordingly, the inner member 62 is stopped on the outer member 61 at an arbitrary position in the axial direction, and can maintain the state thereof. Further, in a case in which the inner member 62 is received in the outer member 61 to a deep position, a part of the radiation source-side arm 63 also enters the outer member 61 in a state in which the longitudinal direction of the radiation source-side arm 63 is aligned with the longitudinal direction of the inner member 62. In a case in which a part of the radiation source-side arm 63 is received in the outer member 61 in this way, the radiation source-side arm 63 cannot revolve about the revolution axis AX4.

From the above, even in the case of the arm unit 200, the radiation source-side arm 63 cannot revolve in a state in which the body-side part of the arm unit including the outer member 61 and the inner member 62 is shorter than a predetermined length. That is, the outer member 61 forms revolution regulating unit in a case in which the length of the outer member 61 is set to the "predetermined length" in this structure. In this case, the length of the body-side part of the arm unit to be compared with the "predetermined length" is a length from the proximal end of the outer member 61 to the distal end of the inner member 62. For convenience sake, this rule is same even in a case in which the distal end of the inner member 62 is positioned in the outer member 61.

Figure 16:
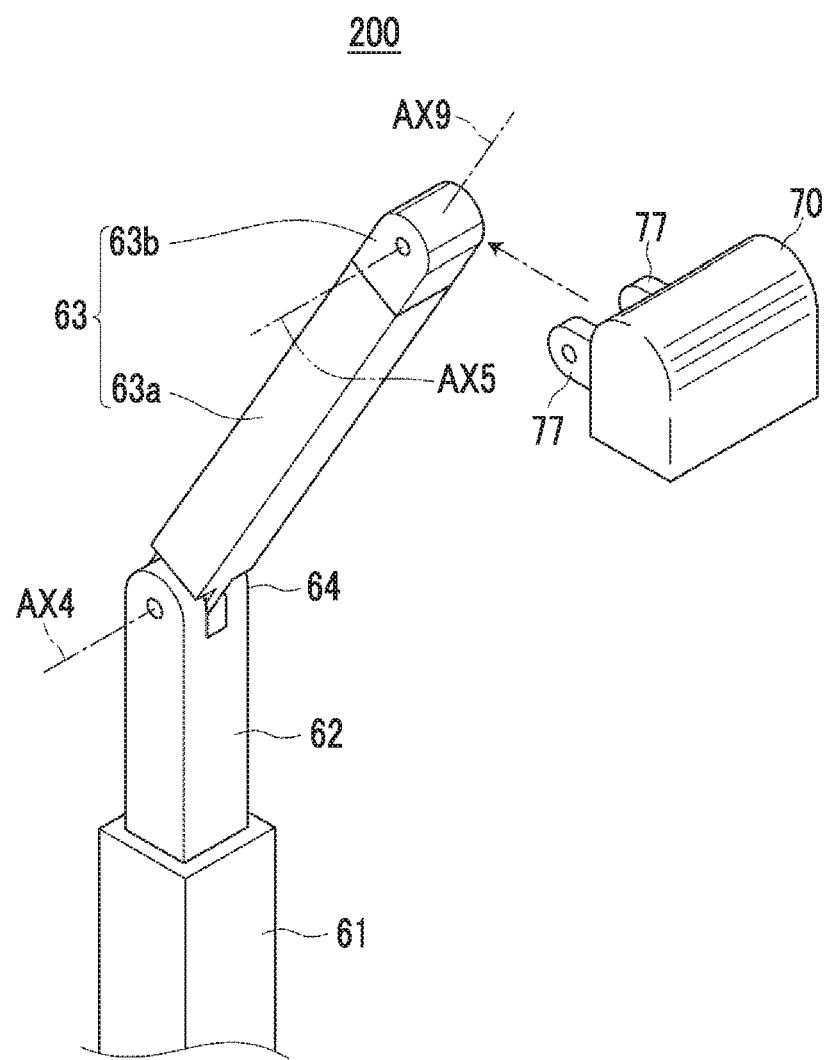
FIG. 16 is a perspective view showing still another example of the arm unit that can be applied to the radiographic imaging apparatus of the invention.

In the structure of FIG. 16, the outer member 61 of the body-side part of the arm unit is disposed so that the longitudinal direction of the outer member 61 is a direction perpendicular to the apparatus-placement surface 2 (see FIG. 2 and the like). Further, the radiation source-side arm 63 includes an elongated part 63a that is relatively long and a distal end part 63b that is connected to the distal end of the elongated part 63a and is relatively short. The distal end part 63b is connected to the elongated part 63a so as to be rotatable about a rotation axis AX9 parallel to the longitudinal direction of the radiation source-side arm 63. Furthermore, the radiation source 70 is connected to the distal end part 63b so as to be oscillatable about an oscillation axis AX5 in a state in which the distal end part 63b is interposed between two support members 77.

Since the radiation source 70, which is mounted on the radiation source-side arm 63 as described above, oscillates as described above and is rotatable about the rotation axis AX9 together with the distal end part 63b, the radiation source 70 is advantageous for the setting of a radiation-irradiation direction to various directions.

Figure 17:
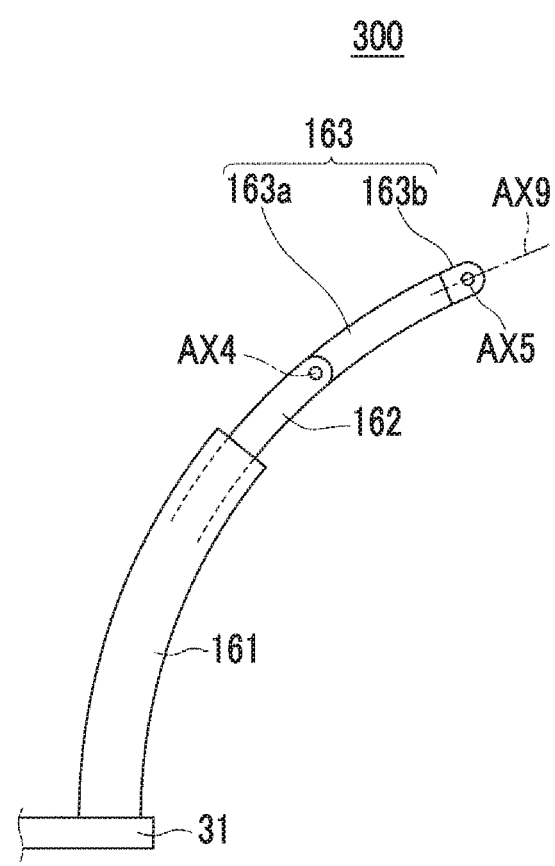
FIG. 17 is a side view showing yet another example of the arm unit that can be applied to the radiographic imaging apparatus of the invention.

In the radiographic imaging apparatus of the invention, the arm unit may be formed in a curved shape. FIG. 17 is a side view showing an example of the arm unit that is formed in the curved shape. An arm unit 300 of FIG. 17 includes an outer member 161, an inner member 162, an elongated part 163a, and a distal end part 163b, which are formed to have the same structures as the outer member 61, the inner member 62, the elongated part 63a, and the distal end part 63b of the arm unit 200 of FIG. 16, except that the arm unit 300 is curved. Further, a radiation source-side arm 163 includes the elongated part 163a and the distal end part 163b. Furthermore, although not shown, a structure for mounting the radiation source 70 on the distal end part 163b is also the same as that of the arm unit 200 of FIG. 16.

In this case, the inner member 162 and the radiation source-side arm 163 are received in the outer member 161 in a state in which the curved longitudinal direction of the inner member 162 is aligned with the curved longitudinal direction of the radiation source-side arm 163. For example, the tubular member 51, the body-side arm 52, and the radiation source-side arm 53 shown in FIG. 3 may be formed in a curved shape. Even in that case, the body-side arm 52 and the radiation source-side arm 53 are received in the tubular member 51 in a state in which the curved longitudinal direction of the body-side arm 52 is aligned with the curved longitudinal direction of the radiation source-side arm 53.

Further, a structure in which the distal end part 163b is rotatable about a rotation axis AX9 parallel to the longitudinal direction of the radiation source-side arm 163 is also the same as that of the arm unit 200 of FIG. 16. More exactly, "the longitudinal direction of the radiation source-side arm 163" in this case is the tangential direction of an end portion, which is mounted on the radiation source, of the curved arm. Furthermore, in a case in which the radiation source is mounted on the arm through an object not having a "longitudinal" direction, for example, a spherical joint or the like, the longitudinal direction of the object is prescribed except for the arm.

What is claimed is:

1. A radiographic imaging apparatus comprising:
a leg unit that is configured to travel on an apparatus-placement surface by a wheel unit;
a body unit that is held on the leg unit;
an arm unit that is connected to the body unit and is configured to protrude upward from the body unit; and
a radiation source that is mounted on the arm unit,
wherein the arm unit includes a body-side part that is configured to extend and retract in a direction of the protruding of the arm unit and is connected to the body unit, and a radiation source-side part on which the radiation source is mounted,
the radiation source-side part is connected to a distal end side of the body-side part so as to be revolvable in a direction where an angle between the radiation source-side part and the body-side part changes, and
a revolution regulating unit configured to allow the radiation source-side part not to revolve in a state in which the body-side part is shorter than a predetermined length is provided,
wherein the revolution regulating unit is formed of a tubular member of which a proximal end is connected to the body unit, and
the tubular member is configured to receive the body-side part and the radiation source-side part of which a longitudinal direction is aligned with a longitudinal direction of the body-side part therein to allow the body-side part and the radiation source-side part to be movable in an axial direction thereof, and the radiation source-side part is set to a length that allows the radiation source-side part to get out of the tubular member in a case in which the body-side part extends to a length equal to or longer than the predetermined length.

2. The radiographic imaging apparatus according to claim 1,
wherein the body-side part of the arm unit is configured in a state in which the longitudinal direction of the body-side part extends in a direction perpendicular to the apparatus-placement surface.

3. The radiographic imaging apparatus according to claim 1,
wherein the radiation source is configured to be rotatable about an axis parallel to the longitudinal direction of the radiation source-side part.

4. The radiographic imaging apparatus according to claim 1,
wherein the wheel unit is formed of a revolving caster.

5. The radiographic imaging apparatus according to claim 1,
wherein the body unit is inclined to a state in which an upper end of the body unit is closer to the radiation source than a lower end of the body unit.

6. The radiographic imaging apparatus according to claim 1,
wherein the wheel unit includes brake unit.

7. A radiographic imaging apparatus comprising:
a leg unit that is configured to travel on an apparatus-placement surface by a wheel unit;
a body unit that is held on the leg unit;
an arm unit that is connected to the body unit and is configured to protrude upward from the body unit; and
a radiation source that is mounted on the arm unit,
wherein the arm unit includes a body-side part that is configured to extend and retract in a direction of the protruding of the arm unit and is connected to the body unit, and a radiation source-side part on which the radiation source is mounted,
the radiation source-side part is connected to a distal end side of the body-side part so as to be revolvable in a direction where an angle between the radiation source-side part and the body-side part changes, and
a revolution regulating unit configured to allow the radiation source-side part not to revolve in a state in which the body-side part is shorter than a predetermined length is provided,
wherein the body-side part of the arm unit includes a tubular outer member of which a proximal end is connected to the body unit and an inner member which is received in the outer member so as to be movable in an axial direction and the radiation source-side part is revolvably connected to a distal end side thereof, and
the outer member is configured to receive the inner member and the radiation source-side part of which a longitudinal direction is aligned with a longitudinal direction of the inner member therein to allow the inner member and the radiation source-side part to be movable in an axial direction thereof, and forms the revolution regulating unit in a case in which the outer member is set to the same length as the predetermined length.

8. The radiographic imaging apparatus according to claim 7,
wherein the body-side part of the arm unit is configured in a state in which the longitudinal direction of the body-side part extends in a direction perpendicular to the apparatus-placement surface.

9. A radiographic imaging apparatus comprising:
a leg unit that is configured to travel on an apparatus-placement surface by a wheel unit;
a body unit that is held on the leg unit;
an arm unit that is connected to the body unit and is configured to protrude upward from the body unit; and
a radiation source that is mounted on the arm unit,
wherein the arm unit includes a body-side part that is configured to extend and retract in a direction of the protruding of the arm unit and is connected to the body unit, and a radiation source-side part on which the radiation source is mounted,
the radiation source-side part is connected to a distal end side of the body-side part so as to be revolvable in a direction where an angle between the radiation source-side part and the body-side part changes, and
a revolution regulating unit configured to allow the radiation source-side part not to revolve in a state in which the body-side part is shorter than a predetermined length is provided,
wherein the revolution regulating unit is formed of a tubular member of which a proximal end is connected to the body unit, and
the tubular member is configured to receive the body-side part and the radiation source-side part of which a longitudinal direction is aligned with a longitudinal direction of the body-side part therein to allow the body-side part and the radiation source-side part to be movable in an axial direction thereof, and the radiation source-side part is set to a length that allows the radiation source-side part to get out of the tubular member in a case in which the body-side part extends to a length equal to or longer than the predetermined length, further comprising a second revolution regulating unit that regulates the radiation source-side part from being positioned to a point lower than a state in which the radiation source-side part is parallel to the apparatus-placement surface.

10. The radiographic imaging apparatus according to claim 9,
wherein the radiation source is configured to be rotatable about an axis parallel to the longitudinal direction of the radiation source-side part.

11. A radiographic imaging apparatus comprising:
a leg unit that is configured to travel on an apparatus-placement surface by a wheel unit;
a body unit that is held on the leg unit;
an arm unit that is connected to the body unit and is configured to protrude upward from the body unit; and
a radiation source that is mounted on the arm unit,
wherein the arm unit includes a body-side part that is configured to extend and retract in a direction of the protruding of the arm unit and is connected to the body unit, and a radiation source-side part on which the radiation source is mounted,
the radiation source-side part is connected to a distal end side of the body-side part so as to be revolvable in a direction where an angle between the radiation source-side part and the body-side part changes, and
a revolution regulating unit configured to allow the radiation source-side part not to revolve in a state in which the body-side part is shorter than a predetermined length is provided,
wherein the radiation source is configured to be oscillatable in a direction where an elevation angle of a radiation-emission axis is changed, and is provided with oscillating-position fixing unit configured to fix an oscillating position of the radiation source, and
wherein in a case in which the fixing of the oscillating position of the radiation source performed by the oscillating-position fixing unit is released, the radiation source is configured to take an oscillating position at which the radiation-emission axis is lowered by an action of its own weight of the radiation source in comparison with a case in which the oscillating position of the radiation source is fixed.

12. The radiographic imaging apparatus according to claim 11,
wherein the body unit is inclined to a state in which an upper end of the body unit is closer to the radiation source than a lower end of the body unit.

* * * * *